United States Patent [19]

Jenck et al.

[11] Patent Number: 4,668,824

[45] Date of Patent: May 26, 1987

[54] PREPARATION OF TRI-(M-SULFOPHENYL)-PHOSPHINE

[75] Inventors: Jean Jenck, Chalampe; Didier Morel, Lyons, both of France

[73] Assignee: Rhone-Poulenc Recherches, Courbevoie, France

[21] Appl. No.: 635,829

[22] Filed: Jul. 30, 1984

[30] Foreign Application Priority Data

Aug. 3, 1983 [FR] France .................. 83 12776

[51] Int. Cl.⁴ .............................. C07F 9/53
[52] U.S. Cl. ........................ 568/15; 568/13; 568/454
[58] Field of Search ................. 568/13, 15

[56] References Cited

U.S. PATENT DOCUMENTS

| | | | |
|---|---|---|---|
| 4,248,802 | 2/1981 | Kuntz | 568/454 |
| 4,346,236 | 8/1982 | Lee | 568/15 |
| 4,376,870 | 3/1983 | Christopfel et al. | 568/15 |
| 4,394,322 | 7/1983 | Beach et al. | 568/13 X |
| 4,507,247 | 3/1985 | Beach et al. | 568/15 X |

FOREIGN PATENT DOCUMENTS 3235030  3/1984  Fed. Rep. of Germany ........ 568/13

OTHER PUBLICATIONS

Chemical Abstracts, 87, 101944n (1977).
Chemical Abstracts, 101, 55331t (1984).

*Primary Examiner*—Helen M. S. Sneed
*Attorney, Agent, or Firm*—Burns, Doane, Swecker & Mathis

[57] ABSTRACT

Essentially pure tri-(m-sulfophenyl)-phosphine, well suited as a ligand for the formation of, e.g., rhodium-based olefin hydroformylation catalysts, is facilely prepared by (i) sulfonating triphenylphosphine with oleum, $H_2SO_4/SO_3$, wherein the temperature of sulfonation ranges from 15° to about 25° C., the molar ratio of $SO_3$/triphenylphosphine is at least 8, and the amount by weight of $SO_3$ in the mixture ($SO_3+H_2SO_4+$triphenylphosphine) at the beginning of said sulfonation reaction is at least 33%; and (ii) thence terminating said sulfonation reaction via hydrolysis of the reaction mixture.

12 Claims, 2 Drawing Figures

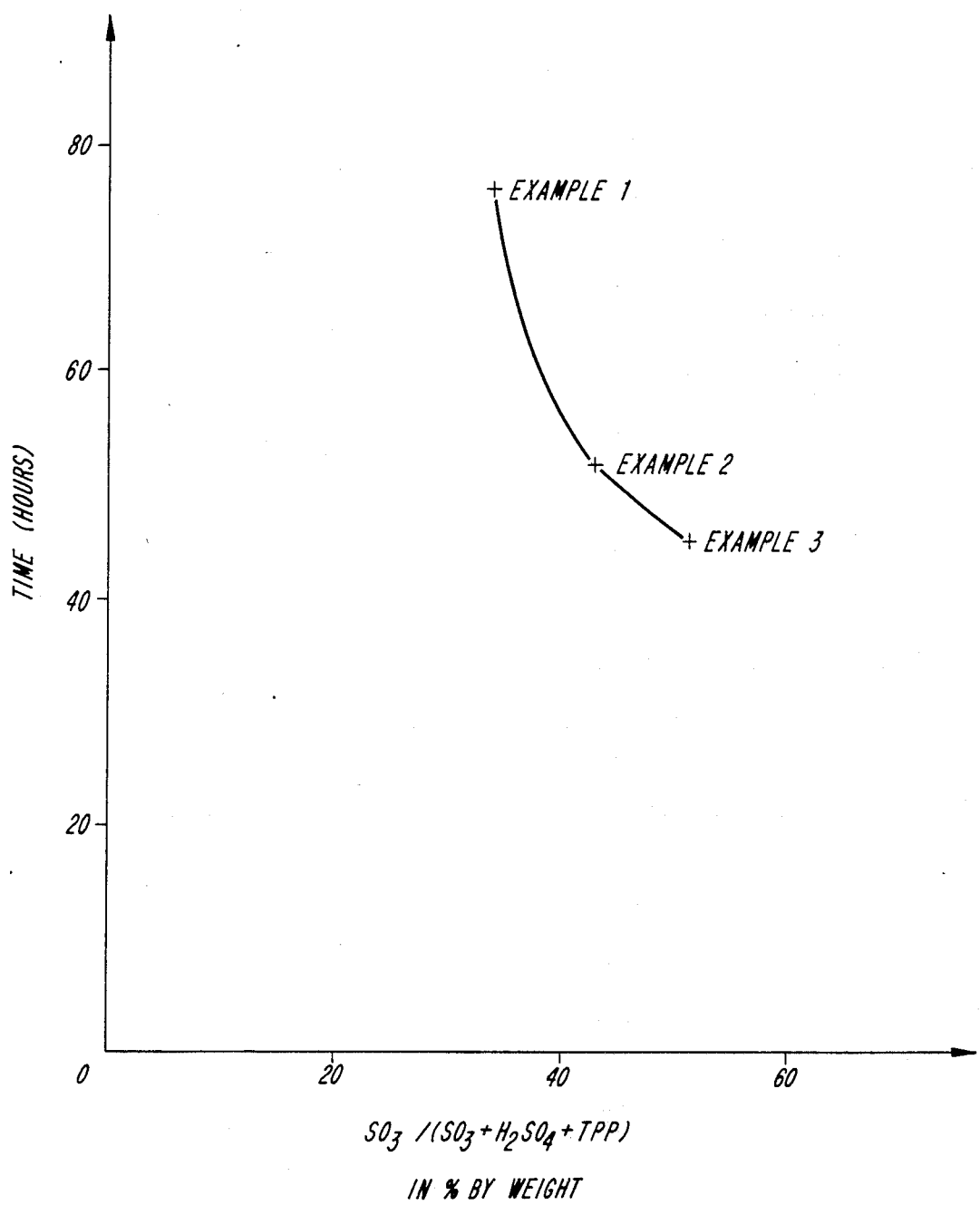

PREPARATION OF TRI-(M-SULFOPHENYL)-PHOSPHINE

BACKGROUND OF THE INVENTION

1. Field of the Invention:

The present invention relates to an improved process for the preparation of tri-(m-sulfophenyl)-phosphine.

2. Description of the Prior Art:

Tri-(m-sulfophenyl)-phosphine (hereinafter referred to as TPPTS) is a known compound useful as a water-soluble ligand permitting the formation of complexes with transition metals, for example rhodium, in water, and such solutions are well adapted as catalysts for the synthesis of aldehyde compounds by hydroformylation of olefins, as described in French Pat. No. 2,314,910.

A synthesis of TPPTS is also described in French Pat. No. 2,314,910. In Example 1 of this patent, the subject compound is prepared in the form of its sodium salt by sulfonation of triphenylphosphine (hereinafter referred to as TPP) utilizing oleum containing 20% by weight of sulfur trioxide ($SO_3$). This gives mono-, di- and trisulfonated triphenylphosphine (hereinafter referred to as TPPMS, TPPDS and TPPTS, respectively) mixed with the oxides of these three compounds (the oxides being hereinafter referred to as OTPPMS, OTPPDS and OTPPTS, also respectively).

The sulfonation reaction is thereafter terminated by diluting the reaction mixture with water. This provides a hydrolysate which is rich in sulfuric acid and contains the sulfonated triphenylphosphine in the acidic form.

To isolate the latter compound in the form of a neutral salt, the hydrolysate is neutralized, for example with sodium hydroxide, thereafter the amount of sulfate anion present in the form of sodium sulfate in the aqueous medium is reduced by successive crystallizations, and the sulfonated triphenylphosphine is then crystallized in the form of its sodium salt by adding methanol and ethanol and subsequently evaporating the solvent. If the sulfonation of the triphenylphosphine is carried out at 30° C. for about 20 hours it is possible to isolate, after various successive crystallizations, a mixture containing 80% by weight of the sodium salt of tri-(sulfophenyl)-phosphine and 20% by weight of the sodium salt of tri-(sulfophenyl)-phosphine oxide.

Further, it has been shown in Example 2 of Certificate of Addition No. 2,349,562 to said French Pat. No. 2,314,910 that in the TPPTS obtained in Example 2 of the basic patent, the sulfonate substitution is in the meta-position.

However, this mode of synthesis of TPPTS has disadvantages. First of all, the neutralization is accompanied by partial oxidation of the phosphine and the resulting oxide is undesirable in that the amount of inert diluent required during the downstream hydroformylation reaction is increased. Moreover, the amount of sodium hydroxide required for neutralization is substantial, since the hydrolysate is rich in $H_2SO_4$. Consequently, the amount of impurities introduced with the sodium hydroxide is large. These impurities, which are subsequently retained in the final product, can interfere with the catalysis. Finally, a mixture of TPPTS, TPPDS and TPPMS is obtained from the sulfonation reaction and these compounds are very difficult to separate.

Published French patent application No. 82/14,862, filed Aug. 31, 1982, describes a process for the preparation of TPPTS which is similar to that described in said French Pat. No. 2,314,910, except that before neutralization with sodium hydroxide, the various sulfonated triphenylphosphines are extracted from the hydrolysate obtained after terminating the sulfonation reaction, by means of an extractant which is in particular selected from among the phosphonic acid esters, such as, for example, dibutyl butylphosphonate or the phosphoric acid esters, such as, for example, tributyl phosphate.

Thus, in Example 4 of said '862 patent application, after the TPP has been sulfonated with oleum containing 20% by weight of $SO_3$ in $H_2SO_4$, treatment with the extractant gives a mixture of 72.9% of TPPTS, 17.1% of TPPDS and 10% of sulfonated triphenylphosphine oxides. It can thus be seen that during the sulfonation stage TPPDS is formed.

It currently appears that among the various sulfonated triarylphosphines described in French Pat. No. 2,214,910, and its Certificate of Addition No. 2,349,562, TPPTS is the best of the ligands for forming a complex with rhodium, and that TPPTS is accordingly superior to TPPMS and to TPPDS.

However, if TPPTS is to provide the best results when used as a ligand, it is necessary that it should be of excellent purity and in particular that it should be free of TPPMS and TPPDS (in which the state of oxidation of the phosphorus is $P^{III}$) and of OTPPMS, OTPPDS and OTPPTS (in which the state of oxidation of the phosphorus is $P^V$).

SUMMARY OF THE INVENTION

Accordingly, a major object of the present invention is the provision of an improved industrial process for the preparation of TPPTS which is conspicuously devoid of those disadvantages and drawbacks to date characterizing the state of this art, and which provides, during the first sulfonation stage, a very high proportion of TPPTS, with the least possible amount of impurities.

Another object of the present invention is the provision of an industrial process for the preparation of TPPTS yielding the highest possible proportion of trisulfonation (the degree of oxidation of the phosphorus being $P^{III}$), while at the same time the degree of oxidation of the sulfonated products (providing materials in which the state of oxidation of the phosphorus is $P^V$) is very low.

Briefly, the present invention features a process for the preparation of TPPTS comprising the sulfonation of TPP with an $H_2SO_4/SO_3$ mixture followed by hydrolysis of the reaction mixture to terminate said sulfonation reaction, such process being characterized in that, in order to obtain a sulfuric acid hydrolysate which is very rich in TPPTS, the sulfonation stage is carried out under the following conditions:

(i) the temperature ranges from 15° to about 25° C.;

(ii) the molar ratio $SO_3$/TPP is greater than or equal to 8; and (iii) the overall amount by weight of $SO_3$ in the mixture of ($SO_3$+TPP+$H_2SO_4$) at the beginning of the reaction is greater than or equal to 33%.

DETAILED DESCRIPTION OF THE INVENTION

Figure 1:
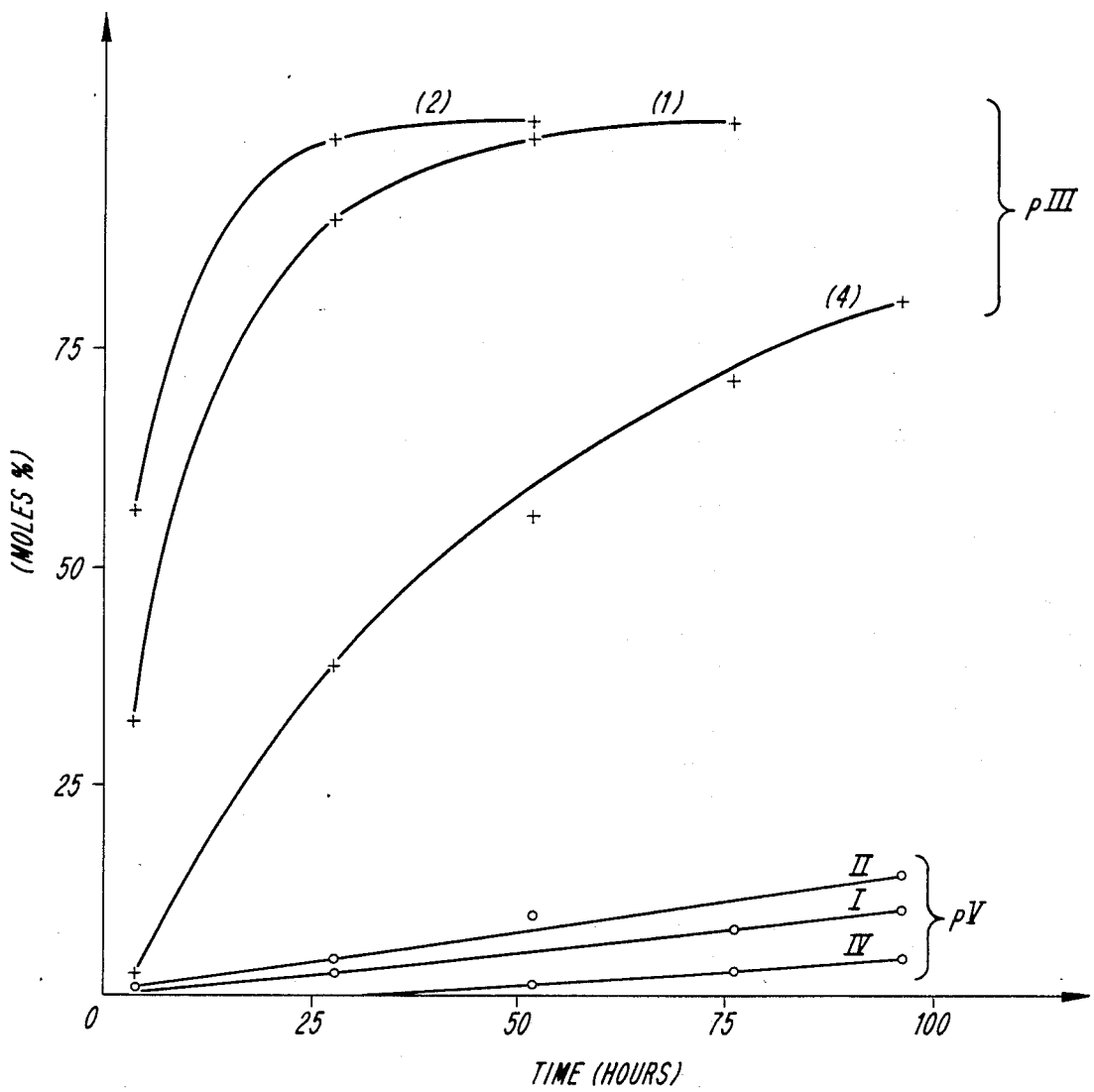

More particularly according to the present invention, to terminate the sulfonation reaction, water is poured into the mixture to hydrate the excess $SO_3$ and give a sulfuric acid hydrolysate which is very rich in TPPTS, namely, a hydrolysate which contains, on the one hand, a very large amount, namely, about 85% or more (in molar % of phosphorus) of sulfonated triphenylphosphine ($p^{III}$), at least 99% (in molar % of phosphorus) of which is TPPTS, and, on the other hand, a low amount, at most 15% (in molar % of phosphorus), of sulfonated triphenylphosphine oxides ($P^V$), the preponderant constituent of which is OTPPTS.

TPPTS can be facilely extracted from the hydrolysate by any known method, for example, by filtering and washing with methanol, as described in Example 7 of French Pat. No. 2,314,910, or preferably by a liquid/liquid extraction as described, for example, in published French Application No. 82/14,862.

According to this latter process, the hydrolysate and the extractant (organic phase) are contacted and the mixture is separated into an organic phase which contains the TPPTS and a small amount of co-extracted sulfuric acid, and an aqueous phase or raffinate which contains the bulk of the sulfuric acid.

Among the preferred extractants suitable therefor, exemplary are the alkyl phosphates, such as, for example, tributyl phosphate, or phosphonates, such as dibutyl butylphosphonate.

This method of purification is particular advantageous because the main impurity present when the sulfonation stage carried out in accordance with the invention is terminated, is essentially OTPPTS and it has been found that the greater part of the sulfonated triphenylphosphine oxide (OTPPTS) present in the hydrolysate is not extracted by the organic extractant and remains in the aqueous phase.

It subsequently remains to separate the TPPTS from the organic phase.

This separation can be effected by contacting the organic phase with water, if it is desired to obtain the TPPTS in the form of the free acid, or with an aqueous solution containing an inorganic or organic cation $M^+$ if it is desired to obtain the TPPTS in salt form, for example with a sodium hydroxide solution.

According to the invention it is necessary that the temperature of sulfonation range from about 15° to 25° C. preferably from 20° to 22° C. If the temperature is below 15° C., the kinetics of the sulfonation reaction are too slow.

If the temperature is above about 25° C., there is a very significant increase in the amount of oxides in the sulfonated products.

It is necessary for the molar ratio $SO_3/TPP$ to be at least equal to 8, preferably ranging from 10 to 14, and more preferably ranging from 10 to 12.

A molar ratio of less than 8 does not result in the disappearance of the TPPMS and TPPDS.

The overall concentration by weight of $SO_3$ in the mixture of ($SO_3 + TPP + H_2SO_4$), hereinafter referred to as the ternary mixture, must be at least 33% at the beginning of the reaction. A concentration of less than 33%, for example 30%, would give high concentrations of TPPMS and TPPDS, or would require an extremely long reaction time.

The sulfonation reaction is effected in the sulfuric acid as the solvent, and the concentration by weight of $H_2SO_4$ in the ternary mixture is advantageously greater than or equal to 15% at the beginning of the reaction (corresponding to the molar ratio of $H_2SO_4/TPP$ greater than or equal to 2.7), such that the viscosity of the mixture should not be too high and the mixture thus remains manageable.

According to a preferred embodiment of the invention, the TPP is first dissolved in sulfuric acid in a proportion of at least 2.7 moles of $H_2SO_4$ per mole of TPP, and thereafter the required concentration by weight of $SO_3$ in the ternary mixture is obtained by adding oleum having a high $SO_3$ content and/or by adding freshly distilled liquid $SO_3$.

The addition of concentrated oleum and/or of liquid $SO_3$ to the sulfuric acid solution is preferably made at a temperature of about 15° C., and thereafter the mixture is preferably brought to a temperature of 20°–22° C. The sulfonation reaction time must be sufficient for all of the TPP starting material to be converted into TPPTS.

This reaction time depends essentially on the temperature of the reaction mixture, and on the $SO_3$ content in the ternary mixture; the lower the temperature and the lower the $SO_3$ content, the longer this time is. One skilled in this art can easily select this time as a function of these parameters.

Thus, for a temperature of 22° C. and an overall $SO_3$ concentration of 50% in the ternary mixture, a reaction time of about 46 hours is sufficient to give more than 99 mole percent of TPPTS (the percentage being based on $P^{III}$). In general, it is desirable to use a reaction time greater than 30 hours, preferably 40 hours. However, if the $SO_3$ concentration is low and close to the limit of about 33%, this time must be on the order of 75 hours. Consequently, it is preferred to use a weight concentration of $SO_3$ in the ternary mixture which is greater than 40%, and which only requires shorter reaction times, on the order of 45 hours or less.

In order to further illustrate the present invention and the advantages thereof, the following specific examples are given, it being understood that same are intended only as illustrative and in nowise limitative.

EXAMPLE 1

80 g of 100% pure sulfuric acid (Prolabo) were introduced into a double-jacketed one-liter glass reactor equipped with a mechanical stirrer and a thermometer and which permitted operation under an argon atmosphere.

The acid was cooled to +15° C. by means of a water/ice bath, under stirring. 20 g of TPP (76.3 millimoles) were introduced slowly at 15° C. over the course of 30 minutes, in 2 g portions (TPP: Fluka, at least 98% pure). This gave a homogeneous solution of TPP in sulfuric acid. 112 g of 65% oleum ($SO_3$ content: 0.91 mole) were then introduced over a time period of 30 minutes at a maximum temperature of 15° C., with good stirring.

The above corresponded to a charge of $SO_3$, $H_2SO_4$ and TPP such that:
(i) $SO_3/TPP = 12$ (molar ratio)
(ii) $SO_3/(SO_3 + H_2SO_4 + TPP) = 34\%$ (by weight)
(iii) $H_2SO_4/(SO_3 + H_2SO_4 + TPP) = 56\%$ (by weight)

The temperature of the reaction mixture was then raised to 22° C. and was maintained thereat for 76 hours.

Thereafter, the bath temperature was lowered to 10° C. and 16.4 g of distilled water (0.9 mole) were solely introduced, while maintaining said temperature of 10° C. throughout, such as to neutralize the exess $SO_3$.

This gave 228.4 g of a solution of sulfonated TPP in sulfuric acid. Analysis of the nuclear magnetic resonance (NMR) spectra ($^{31}P$ nucleus) of the final product on a JEOL SX 100 MHz spectrometer at a frequency of 40.26 MHz evidenced the following composition (in mole % based on P):

(1) TPPTS: 91%; and
(2) Oxides, essentially OTPPTS: 9%.

EXAMPLE 2

The procedures of Example 1 were repeated, except that 20 g of TPP (0.076 mole), 36 g of 100% strength $H_2SO_4$ and 112 g of 65% strength oleum (0.91 mole of $SO_3$) were used, corresponding to a charge of $SO_3$, $H_2SO_4$ and TPP in which:
(i) $SO_3$/TPP = 12 (molar ratio)
(ii) $SO_3$/($SO_3$+$H_2SO_4$+TPP) = 43% (by weight)
(iii) $H_2SO_4$/($SO_3$+$H_2SO_4$+TPP) = 45% (by weight)

The sulfonation reaction was carried out at 22° C. for 52 hours.

This reaction was terminated by adding 16 g of distilled water (0.90 mole) to the reaction mixture.

NMR analysis of the hydrolysate evidenced (in mole %, based on P):
(i) TPPTS: 88.7%
(ii) Oxides, essentially OTPPTS: 11.3%

EXAMPLE 3

The same apparatus as in Example 1 was used. 14.4 g of TPP (0.055 mole) were dissolved in 28.8 g of 98.6% strength $H_2SO_4$ at 20° C. This gave a solution of TPP in $H_2SO_4$ into which 45.87 g of freshly distilled liquid $SO_3$ (0.573 mole) were introduced, over 30 minutes while maintaining the temperature throughout at 15° C. This corresponded to a charge of $SO_3$, $H_2SO_4$ and TPP in which:
(i) $SO_3$/TPP = 10.4 (molar ratio)
(ii) $SO_3$/($SO_3$+$H_2SO_4$+TPP) = 51.5% (by weight)
(iii) $H_2SO_4$/($SO_3$+$H_2SO_4$+TPP) = 32.3% (by weight)

The sulfonation reaction was carried out at 22° C. for 46 hours, under stirring. The excess $SO_3$ was then hydrated by adding 1 g of distilled water to the oleum, maintained at 15° C. NMR analysis ($^{31}$P nucleus) of the resulting mixture evidenced (in mole %, based on P):
(i) TPPTS: 88%
(ii) Oxides, essentially OTPPTS: 12%

COMPARATIVE EXAMPLE 4

Using the same apparatus as in Example 1, 174 g of 20% strength oleum (0.435 mole of $SO_3$) were introduced into the reactor. 10 g of TPP (0.038 mole) were added slowly over a time period of 30 minutes at 15° C., in 1 g portions. A homogenous solution was obtained, which corresponded to a charge of $SO_3$, $H_2SO_4$ and TPP in which:
(i) $SO_3$/TPP = 11.4 (molar ratio)
(ii) $SO_3$/($SO_3$+$H_2SO_4$+TPP) = 19% (by weight)
(iii) $H_2SO_4$/($SO_3$+$H_2SO_4$+TPP) = 76% (by weight)

This was heated to 22° C. and maintained at this temperature for 96 hours.

The temperature was then lowered to 10° C. and 7.1 g of distilled water (0.4300 mole) were then introduced while maintaining this temperature throughout, such as to neutralize the excess $SO_3$.

This gave 191.8 g of a solution of sulfonated TPP in sulfuric acid, analysis of which by NMR ($^{31}$P) evidenced the following composition (in mole %, based on P):
(i) TPPTS: 75.6%
(ii) TPPDS: 18.7%
(iii) Oxides, essentially OTPPDS and OTPPTS: 5.6%

The attained amount of TPPTS, expressed in mole % based on phosphorus, relative to total sulfonated nonoxidized ($P^{III}$) TPP are reported in Table I, in which X denotes the weight ratio $SO_3$/($SO_3$+$H_2SO_4$+TPP).

In FIG. 1 of the attached Figures of Drawing, the proportions of oxidation ($P^V$) and of trisulfonation ($P^{III}$) are plotted as ordinates, in mole % based on phosphorus, against the sulfonation time in hours on the abscissa.

Curves (1) and (I) were obtained from measurements carried out during implementation of Example 1, curves (2) and (II) were obtained from measurements carried out during implementation of Example 2 and curves (4) and (IV) were obtained from measurements carried out during implementation of Comparative Example 4.

FIG. 2 of the attached Figures of Drawing shows, plotted as the ordinate, the time in hours required to give complete trisulfonation as a function of the content of $SO_3$ introduced, plotted on the abscissa as a percentage by weight relative to the ternary mixture [$SO_3$+$H_2SO_4$+TPP].

TABLE I

| Example No. | X (%) | Time in Hours | Total % $P^V$ (x) | Total % $P^{III}$ (x) | of which TPPTS (x) % | TPPDS (x) % |
| --- | --- | --- | --- | --- | --- | --- |
| 1 | 34 | 76 | 9 | 91 | 99+ | 1− |
| 2 | 43 | 52 | 11.3 | 88.7 | 99+ | 1− |
| 3 | 51.5 | 45 | 13 | 87 | 99+ | 1− |

(x): expressed in mole %, based on P
(+): greater than
(−): less than
Molar ratio: $SO_3$/TPP = 12
Sulfonation temperature: 22° C.

COMPARATIVE EXAMPLES 5 to 11

The same apparatus as in Example 1 was used, but the experimental conditions and the results obtained are reported in Table II below, in which x has the same meaning as in Table I.

Comparative Examples 5 to 7 evidence that if the proportion by weight of $SO_3$ in the ternary mixture is too low, it is not possible to achieve the object of the invention (molar proportion, expressed as $P^{III}$, of TPPTS relative to the sulfonated triphenylphosphines obtained: greater than 99%).

Comparative Examples 8 and 9 evidence that it is necessary to have a molar ratio of $SO_3$/TPP at least equal to 8 and preferably at least equal to 10, and Comparative Examples 10 and 11 evidence that too low a molar ratio of $SO_3$/TPP cannot be compensated for by increasing the sulfonation temperature.

TABLE II

| Comparative Example | Molar Ratio $SO_3$/TPP | x (%) | Reaction Temperature | Time in Hours | Total $P^V$ | Total $P^{III}$ | of which TPPMS (x) | TPPDS (x) | TPPTS (x) |
| --- | --- | --- | --- | --- | --- | --- | --- | --- | --- |
| 5 | 12 | 16 | 22 | 192 | 13.9 | 86.1 | 0 | 0 | 0 |
| 6 | 12 | 16 | 26 | 88 | 10.5 | 89.5 | 0 | 14 | 86 |
| 7 | 12 | 16 | 30 | 64.5 | 16.5 | 83.5 | 0⁻ | 12 | 88 |
| 8 | 3.3 | 24.3 | 22 | 44 | 0.5 | 99.5 | NS: 11 66.5 | 22.5 | 0 |

TABLE II-continued

| Comparative Example | Molar Ratio SO₃/TPP | x (%) | Reaction Temperature | Time in Hours | Total $P^V$ | Total $P^{III}$ | of which TPPMS (x) | TPPDS (x) | TPPTS (x) |
|---|---|---|---|---|---|---|---|---|---|
| 9 | 6.8 | 40.4 | 22 | 44 | 15 | 85 | 0 | 56.5 | 38.7 |
| 10 | 3.2 | 23.4 | 30 | 52 | 2.4 | 97.6 | NS: 2.2 / 57.2 | 40 | 0 |
| 11 | 6.3 | 38.3 | 30 | 50 | 14.3 | 85.7 | 10.2 | 85 | 4.8 |

NS: Not sulfonated

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of tri-(m-sulfophenyl)-phosphine, comprising (i) sulfonating triphenylphosphine with oleum, $H_2SO_4/SO_3$, wherein the temperature of sulfonation ranges from 15° to about 25° C., the molar ratio of $SO_3$/triphenylphosphine is at least 8, and the amount by weight of $SO_3$ in the mixture ($SO_3 + H_2SO_4$ + triphenylphosphine) at the beginning of said sulfonation reaction is at least 33%; and (ii) thence terminating said sulfonation reaction via hydrolysis of the reaction mixture.

2. The process as defined by claim 1, wherein the amount by weight of $H_2SO_4$ in the mixture ($SO_3 + H_2SO_4$ + triphenylphosphine) at the beginning of said sulfonation reaction is at least 15%.

3. The process as defined by claim 1, wherein the temperature of sulfonation ranges from 20 to 22° C.

4. The process as defined by claim 1, wherein the molar ratio of $SO_3$/triphenylphosphine ranges from 10 to 14.

5. The process as defined by claim 1, wherein the amount by weight of $SO_3$ in the mixture ($SO_3 + H_2SO_4$ + triphenylphosphine) at the beginning of said sulfonation is at least 40%.

6. The process as defined by claim 5, wherein the sulfonation reaction time is at most 45 hours.

7. The process as defined by claim 1, wherein the reactant triphenylphosphine is in solution in essentially pure $H_2SO_4$ and the reactant $SO_3$ is in the form of concentrated oleum, the form of liquid $SO_3$, or mixture thereof.

8. The process as defined in claim 1, wherein the amount of tri-(m-sulfophenyl)-phosphine comprising the resulting hydrolysate is at least 99%, in moles thereof, based on phosphorus, relative to the total amount of non-oxidized sulfonated triphenylphosphines contained therein.

9. The process as defined by claim 8, wherein the amount of tri-(m-sulfophenyl)-phosphine comprising the resulting hydrolysate is at least 85%, in the moles thereof, based on phosphorus, relative to the total amount of oxidized and non-oxidized sulfonated triphenylphosphines contained therein.

10. The process as defined by claim 1, further comprising separating said tri-(m-sulfophenyl)-phosphine from any oxides comprising the resulting hydrolysate.

11. The process as defined by claim 10, said separation comprising liquid/liquid extraction with an organic extractant.

12. The process as defined by claim 11, said tributylphosphate or organic extractant comprising dibutyl butylphosphonate.

* * * * *